(12) United States Patent
Murayama

(10) Patent No.: US 12,708,793 B2
(45) Date of Patent: Aug. 18, 2026

(54) PHOTOTHERAPY DEVICE, PHOTOTHERAPY METHOD, AND COMPUTER-READABLE RECORDING MEDIUM

(71) Applicant: OLYMPUS CORPORATION, Tokyo (JP)

(72) Inventor: Kazuaki Murayama, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 368 days.

(21) Appl. No.: 18/217,587

(22) Filed: Jul. 2, 2023

(65) Prior Publication Data

US 2023/0347168 A1 Nov. 2, 2023

Related U.S. Application Data

(63) Continuation of application No. PCT/JP2021/016511, filed on Apr. 23, 2021.

(51) Int. Cl.
*A61N 5/06* (2006.01)

(52) U.S. Cl.
CPC ............ *A61N 5/062* (2013.01); *A61N 5/0603* (2013.01); *A61N 2005/0609* (2013.01); *A61N 2005/0663* (2013.01)

(58) Field of Classification Search
CPC ...................................................... A61N 5/062
See application file for complete search history.

(56) References Cited

U.S. PATENT DOCUMENTS 6,128,525 A * 10/2000 Zeng ...................... A61N 5/062 600/317
2008/0188745 A1 8/2008 Chen et al.
2008/0221647 A1* 9/2008 Chamberland ........ A61N 5/062 382/131
2023/0302291 A1* 9/2023 Ishikawa ................ G01N 21/64

FOREIGN PATENT DOCUMENTS

EP 2422688 A1 2/2012
JP 2008-526326 A 7/2008
JP 2012-024283 A 2/2012
JP 2012-115406 A 6/2012
JP 2017-071654 A 4/2017
WO WO-2019215905 A1 * 11/2019 ............ A61B 10/00

OTHER PUBLICATIONS

International Search Report dated Jun. 22, 2021 received in PCT/JP2021/016511.

* cited by examiner

*Primary Examiner* — Lynsey C Eiseman
(74) *Attorney, Agent, or Firm* — Scully, Scott, Murphy & Presser, P.C.

(57) ABSTRACT

A phototherapy device includes: a treatment light emitter configured to emit treatment light for causing a reaction of a drug; a narrow band light emitter configured to emit narrow band light having part of wavelength band of a visible light range; an imager configured to obtain a narrow band light image which is formed using the narrow band light applied onto an application position of the treatment light; a narrow-band-light image variation calculator configured to calculate a time variation between the narrow band light image obtained before an application of the treatment light and the narrow band light image obtained after the application of the treatment light; and a display image generator configured to generate a display image including information based on the calculated variation.

19 Claims, 15 Drawing Sheets

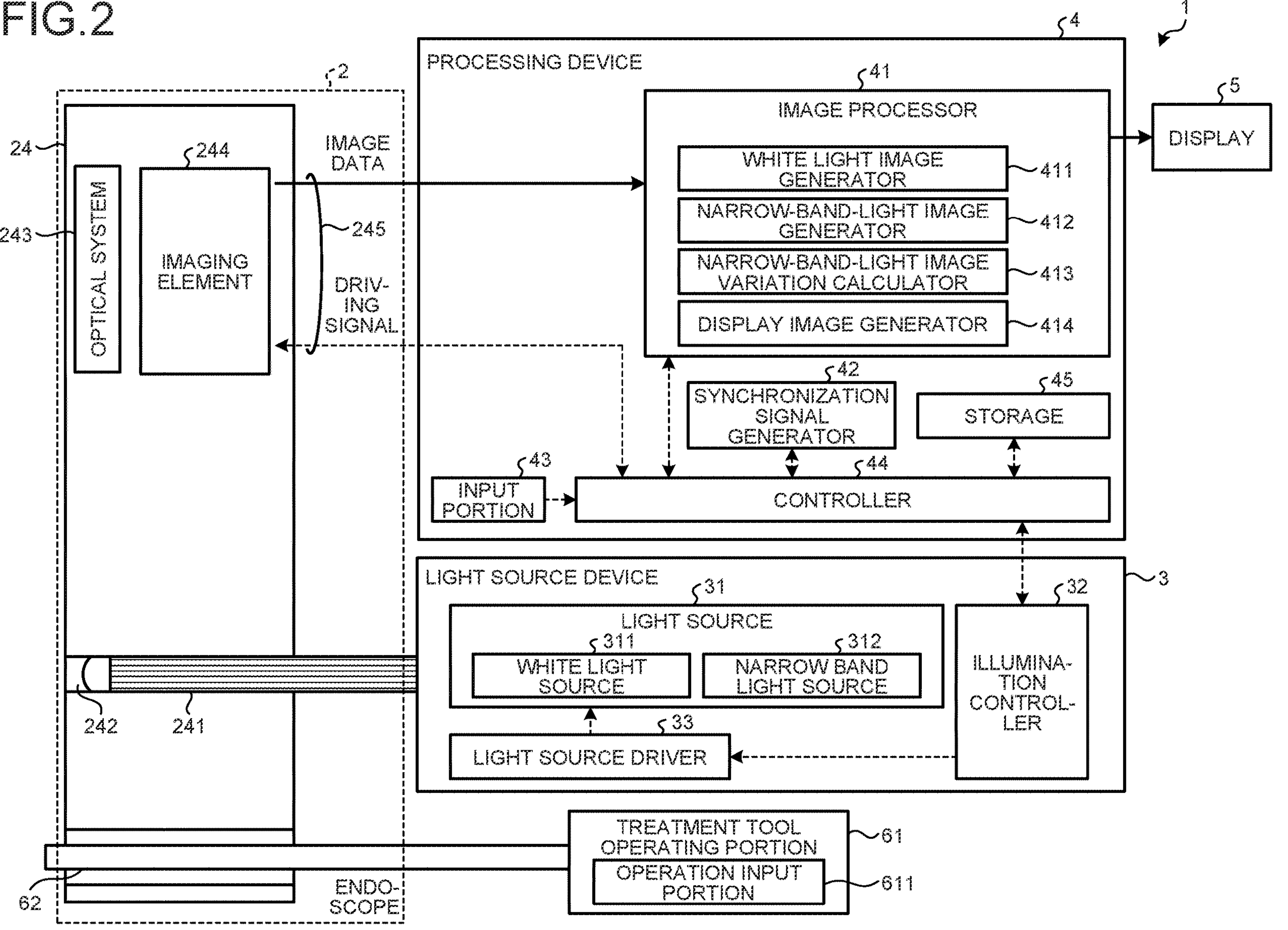

FIG. 2
1
4
PROCESSING DEVICE
41
IMAGE PROCESSOR
WHITE LIGHT IMAGE GENERATOR
411
NARROW-BAND-LIGHT IMAGE GENERATOR
412
NARROW-BAND-LIGHT IMAGE VARIATION CALCULATOR
413
DISPLAY IMAGE GENERATOR
414
5
DISPLAY
42
SYNCHRONIZATION SIGNAL GENERATOR
45
STORAGE
43
INPUT PORTION
44
CONTROLLER
2
24
243
OPTICAL SYSTEM
244
IMAGING ELEMENT
IMAGE DATA
245
DRIV-ING SIGNAL
LIGHT SOURCE DEVICE
3
31
LIGHT SOURCE
311
WHITE LIGHT SOURCE
312
NARROW BAND LIGHT SOURCE
32
ILLUMINA-TION CONTROL-LER
33
LIGHT SOURCE DRIVER
242
241
TREATMENT TOOL OPERATING PORTION
61
OPERATION INPUT PORTION
611
62
ENDO-SCOPE

21
B1
B2
ST
(a)
(b)
(c)
(d)
(e)

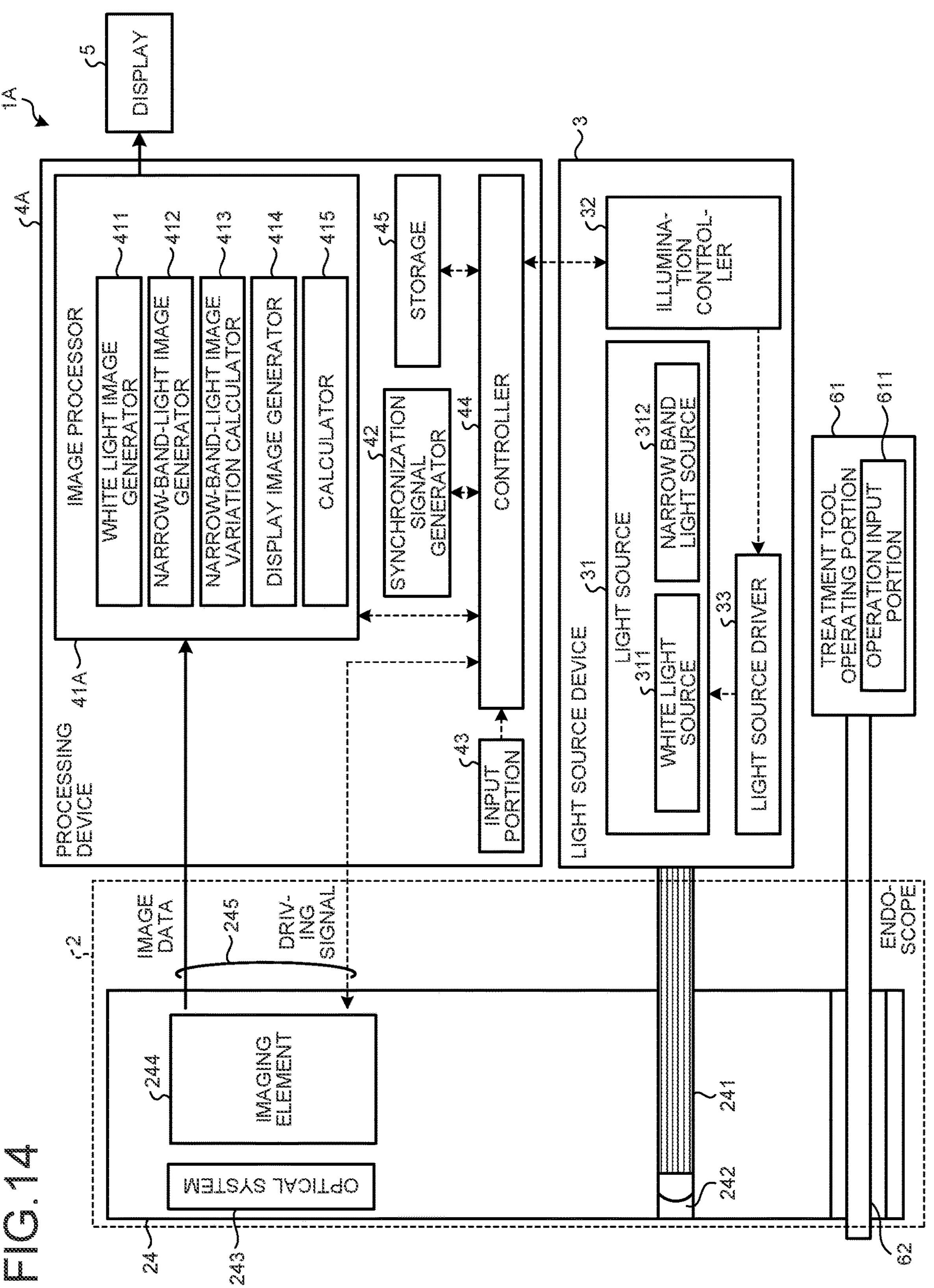
FIG. 14
1A
5
DISPLAY
4A
PROCESSING DEVICE
IMAGE PROCESSOR
411
WHITE LIGHT IMAGE GENERATOR
412
NARROW-BAND-LIGHT IMAGE GENERATOR
413
NARROW-BAND-LIGHT IMAGE VARIATION CALCULATOR
414
DISPLAY IMAGE GENERATOR
415
CALCULATOR
41A
45
STORAGE
42
SYNCHRONIZATION SIGNAL GENERATOR
44
CONTROLLER
43
INPUT PORTION
3
LIGHT SOURCE DEVICE
31
LIGHT SOURCE
311
WHITE LIGHT SOURCE
312
NARROW BAND LIGHT SOURCE
32
ILLUMINATION CONTROLLER
33
LIGHT SOURCE DRIVER
61
TREATMENT TOOL OPERATING PORTION
611
OPERATION INPUT PORTION
2
ENDOSCOPE
IMAGE DATA
245
DRIVING SIGNAL
244
IMAGING ELEMENT
241
242
OPTICAL SYSTEM
243
24
62

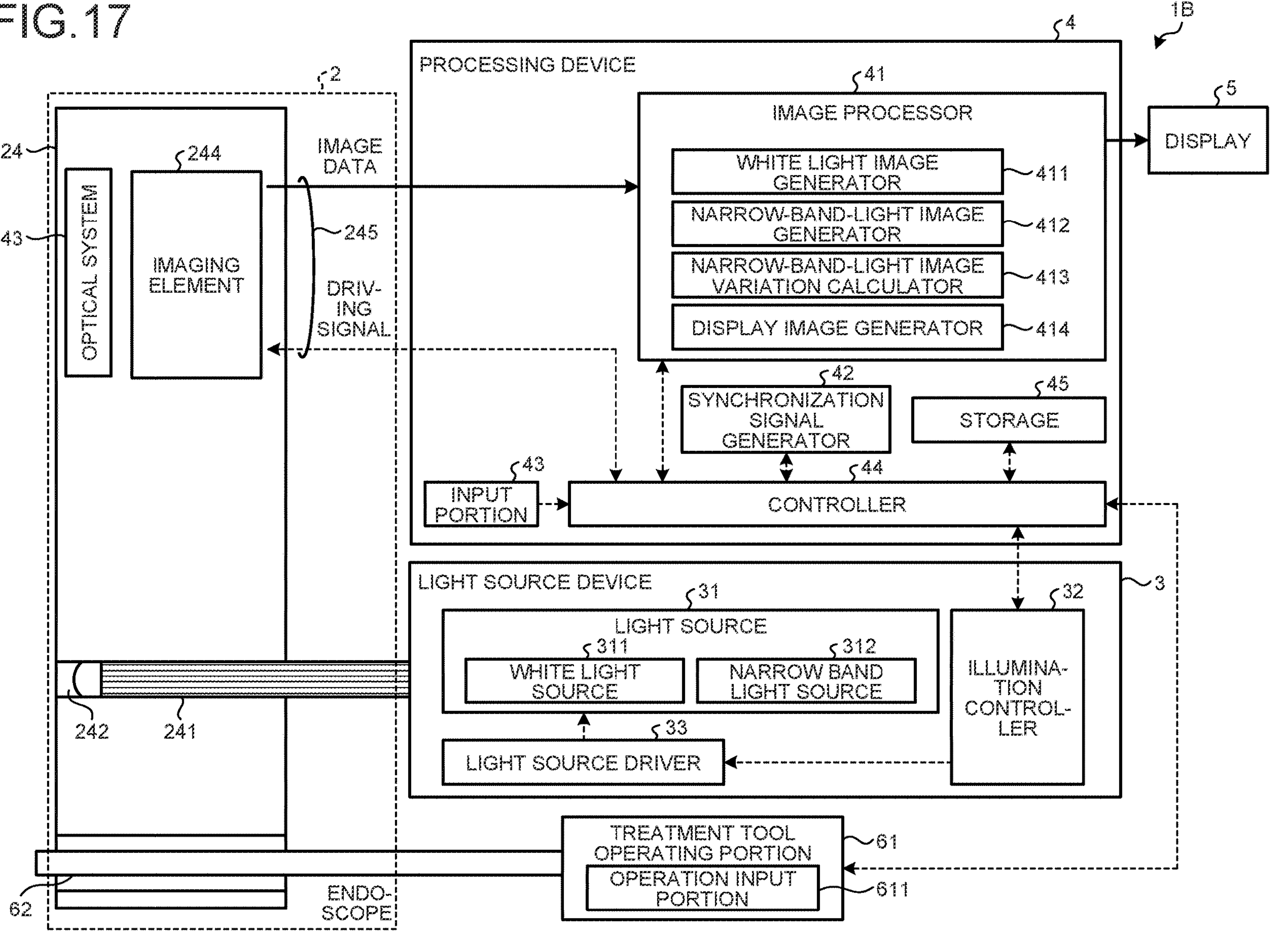
FIG. 17
1B
PROCESSING DEVICE
4
41
IMAGE PROCESSOR
5
DISPLAY
WHITE LIGHT IMAGE GENERATOR
411
NARROW-BAND-LIGHT IMAGE GENERATOR
412
NARROW-BAND-LIGHT IMAGE VARIATION CALCULATOR
413
DISPLAY IMAGE GENERATOR
414
42
SYNCHRONIZATION SIGNAL GENERATOR
45
STORAGE
43
INPUT PORTION
44
CONTROLLER
LIGHT SOURCE DEVICE
3
31
LIGHT SOURCE
311
WHITE LIGHT SOURCE
312
NARROW BAND LIGHT SOURCE
32
ILLUMINATION CONTROLLER
33
LIGHT SOURCE DRIVER
TREATMENT TOOL OPERATING PORTION
61
OPERATION INPUT PORTION
611
2
24
243
OPTICAL SYSTEM
244
IMAGING ELEMENT
IMAGE DATA
245
DRIVING SIGNAL
242
241
62
ENDOSCOPE

PHOTOTHERAPY DEVICE, PHOTOTHERAPY METHOD, AND COMPUTER-READABLE RECORDING MEDIUM

CROSS-REFERENCE TO RELATED APPLICATION

This application is a continuation of International Application No. PCT/JP2021/016511, filed on Apr. 23, 2021, the entire contents of which are incorporated herein by reference.

BACKGROUND

1. Technical Field

The present disclosure relates to a phototherapy device, a phototherapy method, and a computer-readable recording medium.

2. Related Art

In the related art, research is being carried out about photoimmunotherapy (PIT) in which an antibody drug is specifically bound to the protein substance of cancer cells and is activated by the application of a near-infrared light representing the treatment light. As a result, the cancer cells get destroyed, and the cancer is treated (for example, refer to Japanese Patent Application Laid-open No. 2017-71654). The antibody drug, which has the near-infrared light applied thereto, absorbs the light energy; undergoes molecular oscillation; and produces heat. The cancer cells get destroyed due to that heat. At that time, the antibody drug produces fluorescence on account of becoming excited. The intensity of the fluorescence is used as an index of the effect of treatment.

The effect of treatment is believed to have the following three actions.

1. direct damage to cancer cells
2. indirect damage caused by blood flow change
3. indirect damage caused by immune activation It is a known fact that, when the cancer grows, there is an increase in the blood capillaries and the mucous surface turns into a tangled pattern. As a result of "2. indirect damage caused by blood flow change" mentioned above, in the vicinity of the treatment light application area, the blood capillaries on the superficial portion of the mucous membrane undergo changes along with changes in the mucous membrane microstructure. The changes in the blood capillaries on the superficial portion of the mucous membrane and in the mucous membrane microstructure serve as important indexes of confirming the effect of treatment.

SUMMARY

In some embodiments, a phototherapy device includes: a treatment light emitter configured to emit treatment light for causing a reaction of a drug; a narrow band light emitter configured to emit narrow band light having part of wavelength band of a visible light range; an imager configured to obtain a narrow band light image which is formed using the narrow band light applied onto an application position of the treatment light; a narrow-band-light image variation calculator configured to calculate a time variation between the narrow band light image obtained before an application of the treatment light and the narrow band light image obtained after the application of the treatment light; and a display image generator configured to generate a display image including information based on the calculated variation.

In some embodiments, provided is a phototherapy method implemented for applying treatment light, which causes a reaction of a drug, onto a treatment area to confirm an effect of treatment. The phototherapy method includes: obtaining a first narrow band light image formed as a result of applying a narrow band light, which has part of wavelength band of a visible light range, onto a treatment area before an application of the treatment light; obtaining a second narrow band light image formed as a result of applying the narrow band light onto the treatment area after the application of the treatment light; calculating a time variation between the first narrow band light image and the second narrow band light image; and generating a display image including information based on the calculated variation.

In some embodiments, provided is a non-transitory computer-readable recording medium that stores a computer program to be executed by a phototherapy device applying treatment light, which causes a reaction of a drug, onto a treatment area to generate information to be used in confirming an effect of treatment. The program causes the phototherapy device to execute: obtaining a first narrow band light image formed as a result of applying a narrow band light, which has part of wavelength band of a visible light range, onto a treatment area before an application of the treatment light; obtaining a second narrow band light image formed as a result of applying the narrow band light onto the treatment area after the application of the treatment light; calculating a time variation between the first narrow band light image and the second narrow band light image; and generating a display image including information based on the calculated variation.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 2 is a block diagram illustrating an overall configuration of the endoscope system according to the first embodiment of the disclosure;

FIG. 14 is a block diagram illustrating an overall configuration of an endoscope system according to a third embodiment of the disclosure;

FIG. 17 is a block diagram illustrating an overall configuration of an endoscope system according to a sixth embodiment of the disclosure.

DETAILED DESCRIPTION

Figure 1:
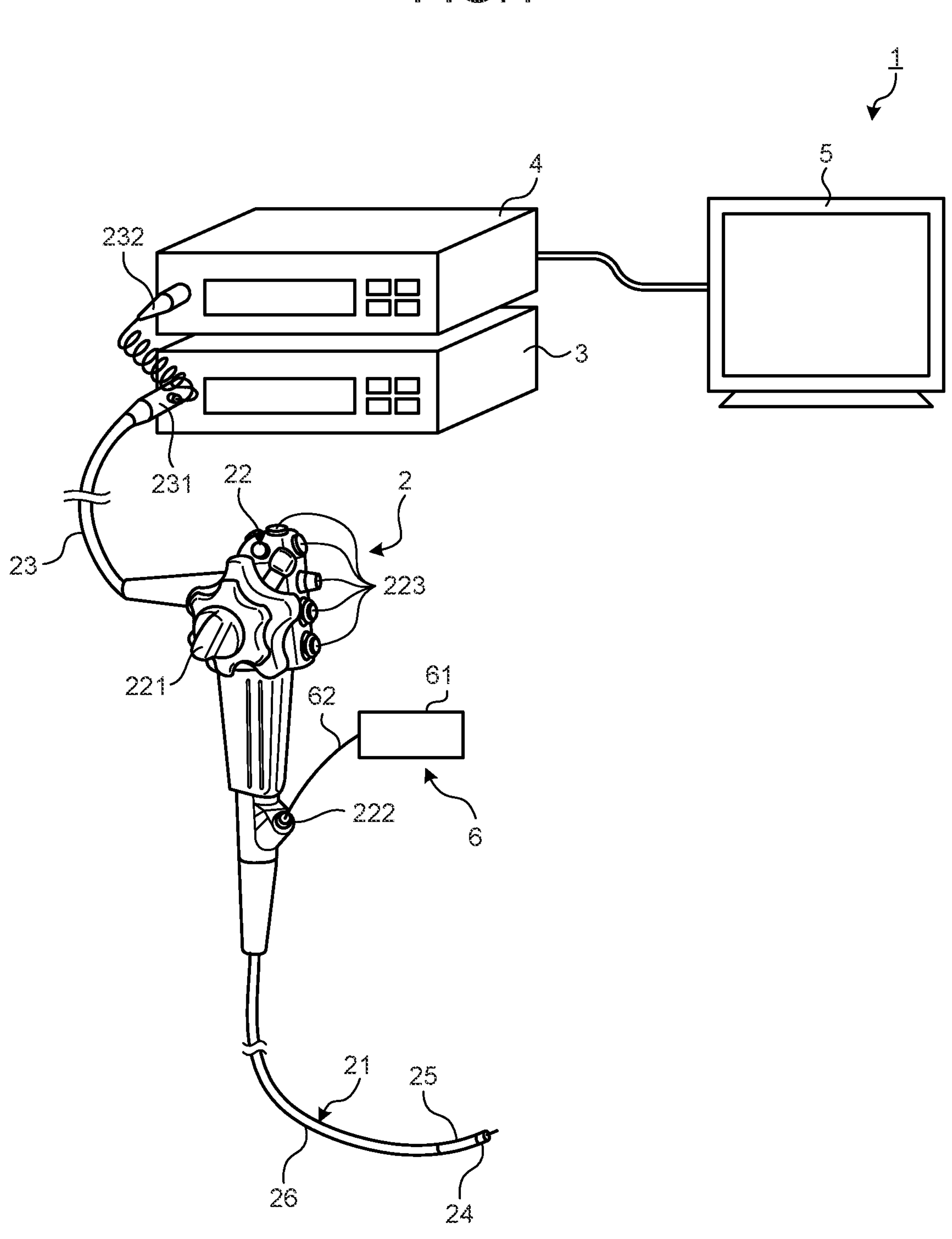
FIG. 1 is a diagram illustrating an overall configuration of an endoscope system according to a first embodiment of the disclosure.

Illustrative embodiments (hereinafter, embodiments) of the disclosure are described below with reference to the accompanying drawings. In the embodiments, as an example of a system that includes a phototherapy device according to the disclosure, the explanation is given about a medical endoscope system that takes images of the inside of a subject, such as a patient, and displays the images. Meanwhile, the disclosure is not limited by the embodiments described below. Moreover, in the drawings, identical constituent elements are referred to by the same reference numerals.

First Embodiment

Figure 3:
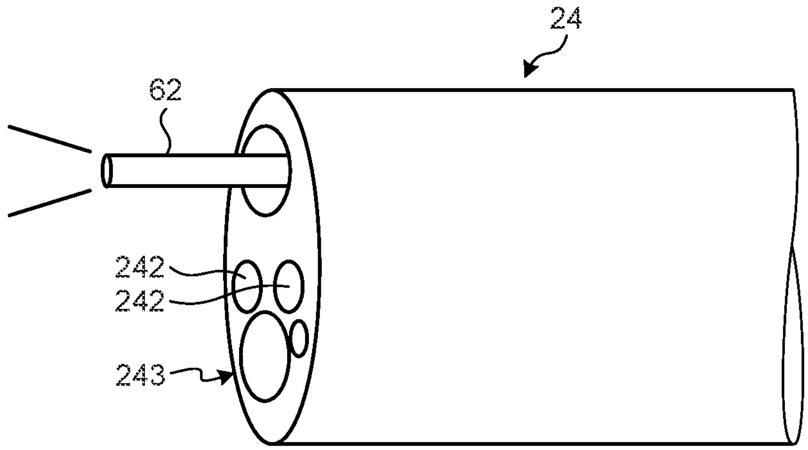
FIG. 3 is a diagram for explaining a front-end configuration of an endoscope according to the first embodiment of the disclosure.

FIG. 1 is a diagram illustrating an overall configuration of an endoscope system according to a first embodiment of the disclosure. FIG. 2 is a block diagram illustrating an overall configuration of the endoscope system according to the first embodiment. FIG. 3 is a diagram for explaining a front-end configuration of an endoscope according to the first embodiment.

An endoscope system 1 illustrated in FIGS. 1 and 2 includes: an endoscope 2 that, when the front end portion thereof is inserted inside the subject, takes in-vivo images of the subject; a light source device 3 that generates an illumination light to be emitted from the front end of the endoscope 2; a processing device 4 that performs predetermined signal processing with respect to imaging signals that are obtained by the endoscope 2 by performing imaging, and that comprehensively controls the overall operations of the endoscope system 1; a display 5 that displays in-vivo images generated as a result of the signal processing performed by the processing device 4; and a treatment tool device 6.

The endoscope 2 includes: a flexible and elongated insertion portion 21; an operating portion 22 that is connected to the proximal end of the insertion portion 21 and that receives input of various operation signals; and a universal cord 23 that extends from the operating portion 22 in the opposite direction to the direction of extension of the insertion portion 21, and that has various built-in cables connected to the light source device 3 and the processing device 4.

The insertion portion 21 includes the following: a front end portion 24 that has a built-in imaging element 244 in which pixels meant for receiving light and generating signals according to photoelectric conversion are arranged in a two-dimensional manner; a freely-bendable curved portion 25 that is made of a plurality of bent pieces; and a flexible tube 26 that is a flexible and long tube connected to the proximal end of the curved portion 25. The insertion portion 21 is inserted into the body cavity of the subject. Then, using the imaging element 244, the insertion portion 21 takes images of the body tissue present at such positions inside the photographic subject up to which the outside light does not reach.

The operating portion 22 includes the following: a bending knob 221 that makes the curved portion 25 bend in the vertical direction and the horizontal direction; a treatment tool insertion portion 222 through which a treatment tool such as a treatment-light application device, biopsy forceps, an electrical scalpel, or an inspection probe is inserted into the body cavity of the subject; and a plurality of switches 223 representing operation input portions that receive input of operation instruction signals regarding the peripheral devices including not only the processing device 4 but also an insufflation unit, a water supply unit, and a screen display control. The treatment tool inserted from the treatment tool insertion portion 222 passes through a treatment tool channel (not illustrated) in the front end portion 24 and comes out from an opening of the front end portion 24 (see FIG. 3).

The universal cord 23 at least has a built-in light guide 241 and a built-in cable assembly 245, which has one or more cables bundled therein. The universal cord 23 is branched at the end portion on the opposite side to the side of connection with the operating portion 22. At the branched end portion of the universal cord 23, a connector 231 is disposed that is detachably attachable to the light source device 3, and a connector 232 is disposed that is detachably attachable to the processing device 4. From the end portion of the connector 231, some part of the light guide 241 extends out. The universal cord 23 propagates the illumination light, which is emitted from the light source device 3, to the front end portion 24 via the connector 231 (the light guide 241), the operating portion 22, and the flexible tube 26. Moreover, the universal cord 23 transmits the image signals, which are obtained as a result of the imaging performed by the imaging element 244 that is disposed in the front end portion 24, to the processing device 4 via the connector 232. The cable assembly 245 includes a signal line for transmitting imaging signals; a signal line for transmitting driving signals meant for driving the imaging element 244; and a signal line for sending and receiving information such as the specific information related to the endoscope 2 (the imaging element 244). In the first embodiment, the explanation is given under the premise that a signal line is used for transmitting electrical signals. Alternatively, a signal line can be used for transmitting optical signals, or can be used for transmitting signals between the endoscope 2 and the processing device 4 in a wireless manner.

The front end portion 24 is made of fiberglass, and includes the following: the light guide 241 that constitutes a light guiding path for the light generated by the light source device 3; an illumination lens 242 that is disposed at the front end of the light guide 241; an optical system 243 that collects light; and the imaging element 244 that is disposed at the image formation position of the optical system 243 and that receives the light collected by the optical system 243, performs photoelectric conversion, and performs predetermined signal processing with respect to electrical signals.

The optical system 243 is configured using one or more lenses. The optical system 243 forms an observation image on the light receiving surface of the imaging element 244. Meanwhile, the optical system 243 can also be equipped with the optical zooming function meant for varying the angle of view and the focusing function meant for varying the focal point.

The imaging element 244 performs photoelectric conversion with respect to the light coming from the optical system 243, and generates electrical signals (image signals). In the imaging element 244, a plurality of pixels, each of which includes a photodiode for storing the electrical charge according to the amount of light and includes a capacitor for converting the electrical charge transferred from the photodiode into a voltage level, are arranged as a two-dimensional matrix. In the imaging element 244, each pixel performs photoelectric conversion with respect to the incoming light coming via the optical system 243 and generates an electrical signal. Then, the imaging element 244 sequentially reads the electrical signals generated by arbitrarily-set target pixels for reading from among a plurality of pixels, and outputs those electrical signals as image signals. The first imaging element **244*a* as well as the second imaging element 244*b*** is configured using, for example, a CCD image sensor (CCD stands for Charge Coupled Device) or a CMOS image sensor (CMOS stands for Complementary Metal Oxide Semiconductor).

Meanwhile, the endoscope 2 includes a memory (not illustrated) that is used to store an execution program and a control program meant for enabling the imaging element 244 to perform various operations, and to store data containing the identification information of the endoscope 2. The identification information contains the specific information (ID), the model year, the specifications information, and the transmission method of the endoscope 2. Moreover, the memory can also be used to temporarily store the image data generated by the imaging element 244.

Given below is the explanation about a configuration of the light source device 3. The light source device 3 includes a light source 31, an illumination controller 32, and a light source driver 33. Under the control of the illumination controller 32, the light source 31 sequentially switches the illumination light and emits it onto the photographic subject (subject).

The light source 31 is configured using light sources and one or more lenses, and emits a light (illumination light) when one of the light sources is driven. The light generated by the light source 31 is emitted from the front end of the front end portion 24 toward the photographic subject via the light guide 241. The light source 31 includes a white light source 311 and a narrow band light source 312. Herein, a light source, the light guide 241, and the illumination lens 242 constitute an emitter. For example, the narrow band light source 312, the light guide 241, and the illumination lens 242 constitute a narrow band light emitter.

The white light source 311 emits the light having the wavelength band of the visible light range (i.e., emits a white light). The white light source 311 is implemented using an LED light source, a laser light source, a xenon lamp, or a halogen lamp.

Figure 4:
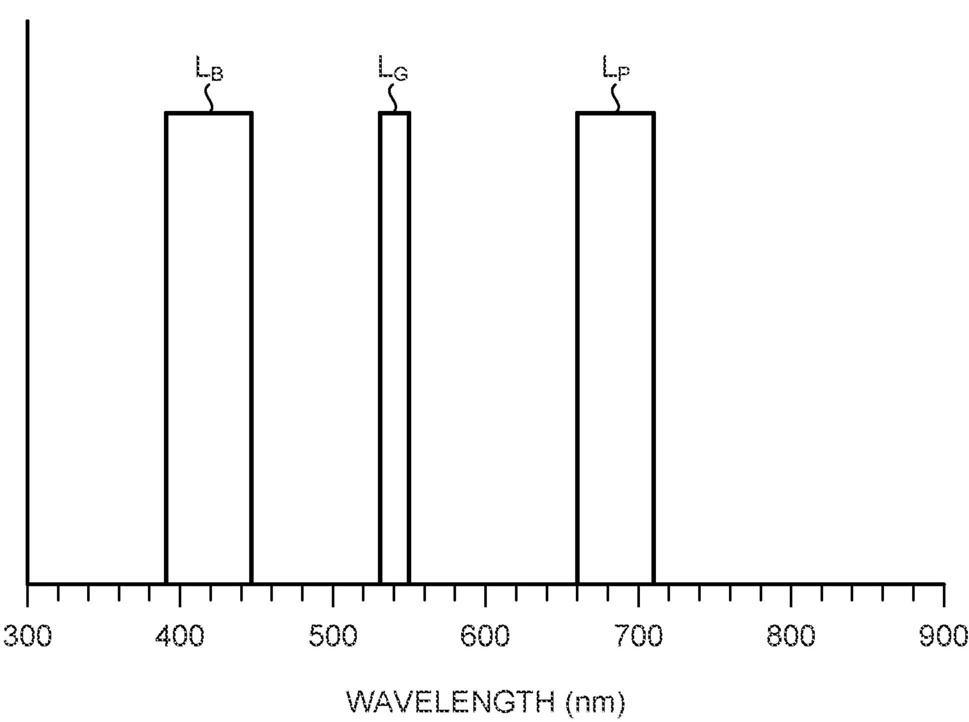
FIG. 4 is a diagram for explaining an example of the wavelength band of a light used as a narrow band light.

The narrow band light source 312 emits a light having some wavelengths or some part of the wavelength band from among the wavelength band of the visual light range. FIG. 4 is a diagram for explaining an example of the wavelength band of the light used as the narrow band light. The narrow band light is made of either one of the following lights or is made of a combination of the following lights: a light $L_B$ having the wavelength band equal to or greater than 390 nm and equal to or smaller than 445 nm; and a light $L_G$ having the wavelength band equal to or greater than 530 nm and equal to or smaller than 550 nm. Examples of the narrow band light include a light that is made of the lights $L_B$ and $L_G$ and that is used in NBI observation (NBI stands for Narrow Band Imaging). In the first embodiment, the explanation is given about the case in which a light made of the lights $L_B$ and $L_G$ is used as the narrow band light. Besides, the narrow band light can be made of either one of the following lights or can be made of a combination of some of the following lights: a light having the wavelength band equal to or greater than 490 nm and equal to or smaller than 590 nm; a light having the wavelength band equal to or greater than 590 nm and equal to or smaller than 620 nm; and a light having the wavelength band equal to or greater 620 nm and equal to or smaller than 780 nm. The narrow band light source 312 is implemented using an LED light source or a laser light source.

Meanwhile, in the case of causing excitation of the antibody drug during photoimmunotherapy, for example, a near-infrared light $L_P$ having the central wavelength of 690 nm is used (for example, the near-infrared light $L_P$ which is illustrated in FIG. 4 and which has the wavelength band equal to or greater than 660 nm and equal to or smaller than 710 nm is used).

Herein, if the light having the wavelength equal to or greater than 390 nm and equal to or smaller than 445 nm is emitted and if the scattering light or the returning light is obtained, then the blood vessels in the superficial portion of the mucous membrane can be visualized with a high degree of contrast. Alternatively, if the light having the wavelength band equal to or greater than 530 nm and equal to or smaller than 550 nm is emitted, or if the light having the wavelength band equal to or greater than 590 nm and equal to or smaller than 620 nm is emitted, or if the light having the wavelength band equal to or greater than 620 nm and equal to or smaller than 780 nm is emitted, and if the scattering light or the returning light is obtained; then the blood vessels in the relatively deeper portion of the mucous membrane can be visualized with a high degree of contrast.

Based on a control signal (modulated light signal) received from the processing device 4, the illumination controller 32 controls the electrical energy to be supplied to the light source 31, controls the light source to be made to emit light, and controls the driving timing of the light source.

Under the control of the illumination controller 32, the light source driver 33 supplies an electrical current to the light source to be made to emit light, and causes the light source 31 to output the light.

Given below is the explanation of a configuration of the processing device 4. The processing device 4 includes an image processor 41, a synchronization signal generator 42, an input portion 43, a controller 44, and a storage 45.

The image processor 41 receives, from the endoscope 2, image data of the illumination light of each color as obtained by the imaging element 244 by performing imaging. If analog image data is received from the endoscope 2, then the image processor 41 performs A/D conversion and generates digital imaging signals. Moreover, if image data in the form of optical signals is received from the endoscope 2, then the image processor 41 performs photoelectric conversion and generates digital image data.

The image processor 41 performs predetermined image processing with respect to the image data received from the endoscope 2, generates an image, and outputs the image to the display 5. Moreover, the image processor 41 sets boundary regions determined based on the image, and calculates the time variation in the fluorescence intensity. The image processor 41 includes a white light image generator 411, a narrow-band-light image generator 412, a narrow-band-light image variation calculator 413, and a display image generator 414.

The white light image generator 411 generates a white light image based on an image formed using a white light.

The narrow-band-light image generator 412 generates a narrow band light image based on an image formed using a narrow band light.

The optical system 243, the imaging element 244, and an image generator constitute an imager. For example, in the case of obtaining an image formed using the illumination of a narrow band light; the optical system 243, the imaging element 244, and the narrow-band-light image generator 412 constitute an imager for obtaining the narrow band light image.

The narrow-band-light image variation calculator 413 calculates the time variation between the narrow band light images that are generated by the narrow-band-light image generator 412 at different timings. The narrow-band-light image variation calculator 413 calculates the amount of variation seen in the photographic subject that is captured in the images.

The display image generator 414 generates an image to be displayed in the display 5. Herein, an image implies an image based on the white light or the narrow band light, or an image indicating the variation between narrow band light images.

The white light image generator 411, the narrow-band-light image generator 412, as well as the display image generator 414 performs predetermined image processing and generates an image. Herein, the predetermined image processing includes synchronization, gray level correction, or color correction. The synchronization represents the operation of achieving synchronization among the image data of the RGB color components. The gray level correction represents the operation of correcting the gray level of the image data. The color correction represents the operation of performing color compensation with respect to the image data. Meanwhile, the white light image generator 411, the narrow-band-light image generator 412, and the display image generator 414 can also perform gain adjustment according to the brightness of an image.

The image processor 41 is configured either using a general-purpose processor such as a processing unit (CPU) or using a dedicated processor such as one of various arithmetic circuits, such as an application specific integrated circuit (ASIC), that implements specific functions. Moreover, the image processor 41 can be configured to include a frame memory for storing R image data, G image data, and B image data.

The synchronization signal generator 42 generates clock signals (synchronization signals) serving as the basis for the operations performed by the processing device 4, and outputs the generated synchronization signals to the light source device 3, the image processor 41, the controller 44, and the endoscope 2. Herein, the synchronization signals generated by the synchronization signal generator 42 include a horizontal synchronization signal and a vertical synchronization signal.

Thus, the light source device 3, the image processor 41, the controller 44, and the endoscope 2 perform operations in synchronization with each other based on the generated synchronization signals.

The input portion 43 is configured using a keyboard, a mouse, switches, or a touch-sensitive panel, and receives input of various signals such as an operation instruction signal that is meant for instructing the operations of the endoscope system 1. Meanwhile, the input portion 43 can also represent switches installed in the operating portion 22, or can be a portable terminal such as an external tablet computer.

The controller 44 performs driving control of the constituent elements including the imaging element 244 and the light source device 3, and performs input-output control of information with respect to the constituent elements. The controller 44 refers to control information data (for example, the reading timing) that is stored in the storage 45 and that is to be used in performing image control, and sends the control information data as driving signals to the imaging element 244 via predetermined signal lines included in the cable assembly 245. Moreover, the controller 44 switches between a normal observation mode meant for observing the images obtained in white light illumination and a narrow band light observation mode meant for observing the images obtained in the illumination of the narrow band light. The controller 44 is configured using a general-purpose processor such as a CPU or using a dedicated processor such as one of various arithmetic circuits, such as an ASIC, that implements specific functions.

The storage 45 is used to store various computer programs meant for causing the endoscope system 1 to perform operations, and to store data containing various parameters required in the operations performed by the endoscope system 1. Moreover, the storage 45 is used to store the identification information of the processing device 4, which contains the specific information (ID), the model year, and the specifications information of the processing device 4.

Moreover, the storage 45 is used to store various computer programs including an image obtaining program that is meant for enabling the processing device 4 to implement an image obtaining method. The computer programs can be recorded for circulation in a computer-readable recording medium such as a hard disk, a flash memory, a CD-ROM, a DVD-ROM, or a flexible disk. Alternatively, the computer programs can be downloaded via a communication network, which is implemented using, for example, an existing public line, or a local area network (LAN), or a wide area network (WAN); and which can be a wired network or a wireless network.

The storage 45 is implemented using a read only memory (ROM) in which various computer programs are installed in advance, and using a random access memory (RAM) or a hard disk in which various operation parameters and data are stored.

The display 5 displays a display image corresponding to the image signal received from the processing device 4 (the image processor 41) via a video cable. The display 5 is configured using a monitor such as a liquid crystal display or an organic electroluminescence (EL) display.

The treatment tool device 6 includes a treatment tool operating portion 61, and includes a flexible treatment tool 62 that extends from the treatment tool operating portion 61. The treatment tool 62 that is used in photoimmunotherapy emits a light for enabling treatment (hereinafter, called the treatment light). The treatment tool operating portion 61 controls the emission of the treatment light from the treatment tool 62. The treatment tool operating portion 61 includes an operation input portion 611 that is configured using, for example, switches. In response to an input (for example, in response to the pressing of a switch) with respect to the operation input portion 611, the treatment tool operating portion 61 causes the treatment tool 62 to emit the treatment light. Meanwhile, in the treatment tool device 6, the light source that emits the treatment light either can be installed in the treatment tool 62 or can be installed in the treatment tool operating portion 61. The light source is implemented using a semiconductor laser or a light emitting diode (LED). For example, in the case of implementing photoimmunotherapy, the treatment light has the wavelength band equal to or greater than 680 nm and, for example, has the central wavelength of 690 nm (for example, the light $L_P$ illustrated in FIG. 4).

Herein, the illumination optical system included in the treatment tool 62 can be configured to enable varying the application range of the treatment light. For example, under the control of the treatment tool operating portion 61, the illumination optical system can be configured either using an optical system in which the focal distance can be varied or using a digital micromirror device (DMD); and it is possible to vary the spot diameter of the light applied onto the subject and to vary the shape of the application range.

Figure 5:
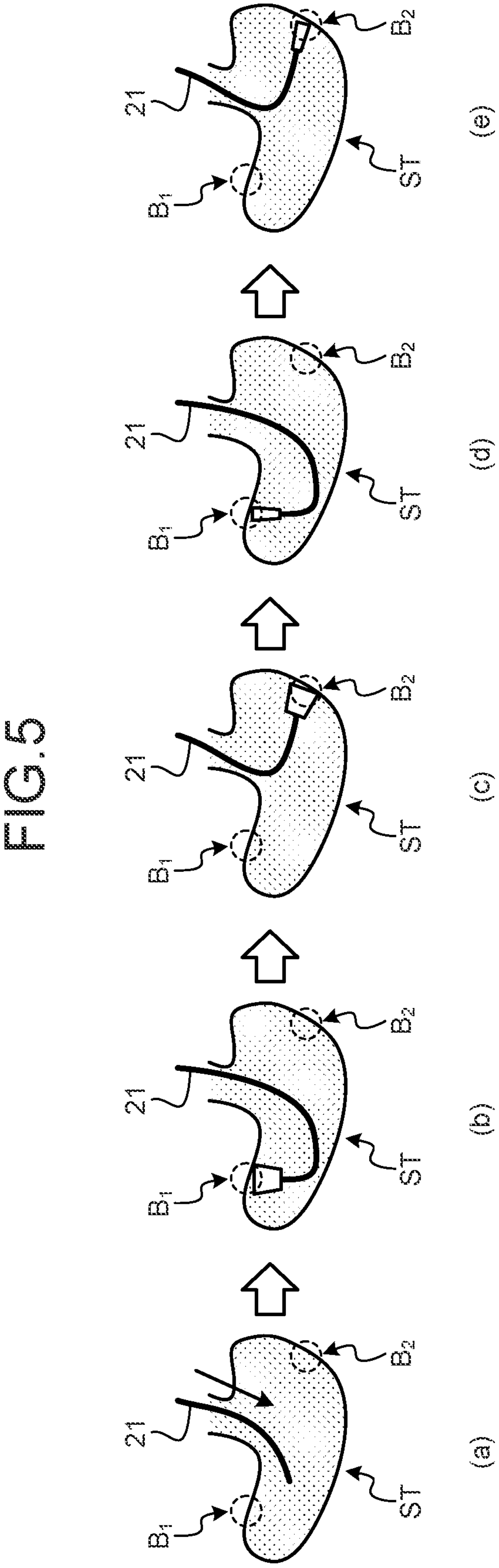
FIG. 5 is a diagram illustrating an exemplary flow of the treatment performed using the endoscope according to the first embodiment of the disclosure.
Figure 6:
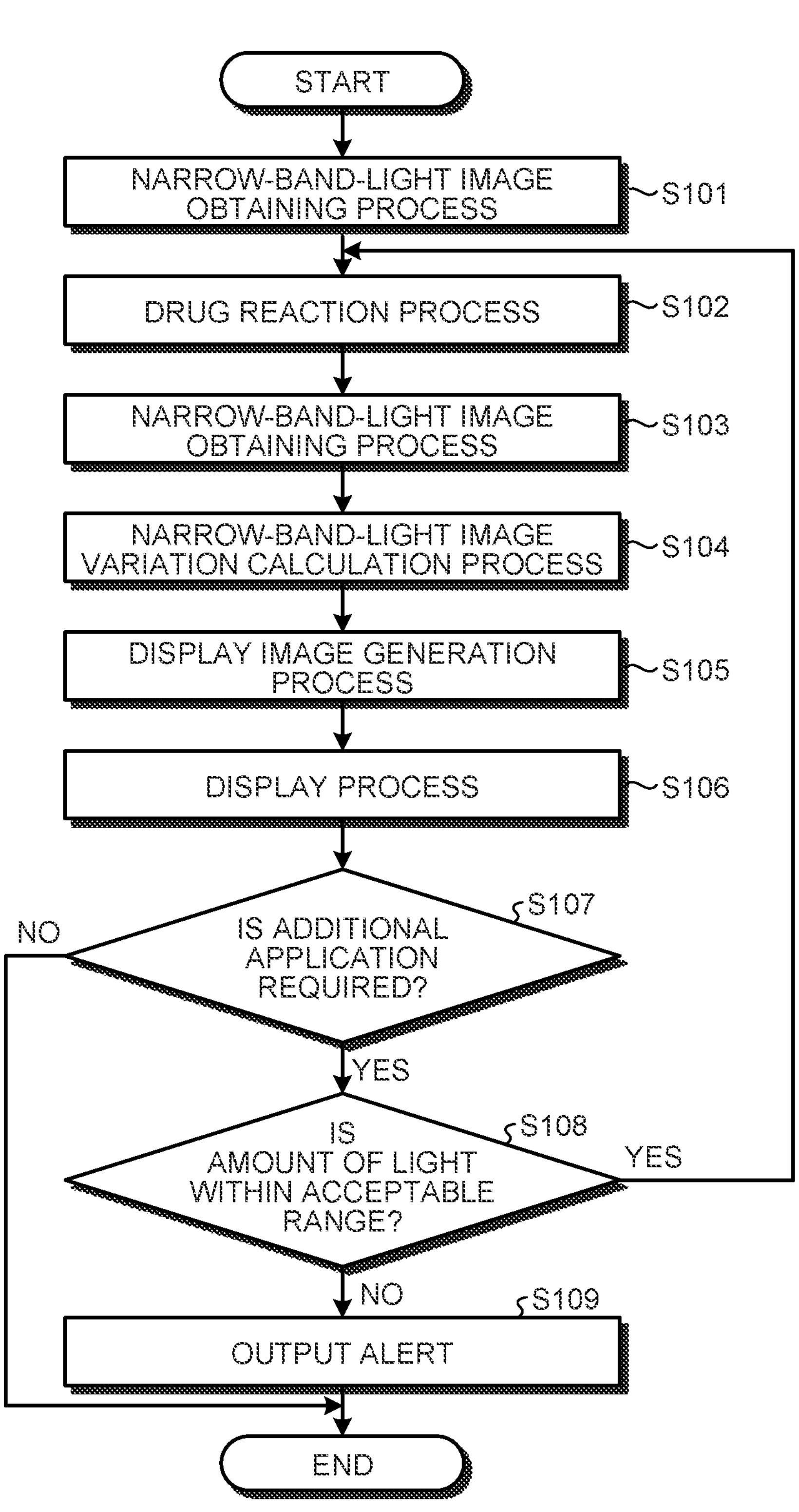
FIG. 6 is a flowchart for explaining an example of the operations performed by a processing device according to the first embodiment.

Explained below with reference to FIGS. 5 and 6 is the flow of the treatment performed using the endoscope 2. FIG. 5 is a diagram illustrating an exemplary flow of the treatment performed using the endoscope according to the first embodiment of the disclosure. In FIG. 5 is illustrated an example of implementing photoimmunotherapy; and the insertion portion 21 is inserted into a stomach ST for carrying out the treatment.

Firstly, the operator inserts the insertion portion 21 into the stomach ST (see (a) in FIG. 5). At that time, the operator instructs the light source device 3 to emit the white light and, while observing the white light image that captures the inside of the stomach ST and that is displayed in the display 5, searches for the treatment position. Herein, it is assumed that the treatment is carried out for tumors $B_1$ and $B_2$ representing the treatment targets. At that time, an antibody drug is administered to the tumors $B_1$ and $B_2$ representing the target body parts for treatment. The antibody drug can be administered using the endoscope 2 or using some other device, or the patient can be asked to take the antibody drug.

The operator observes the white light image and decides on the region that includes the tumors $B_1$ and $B_2$ as the application region. Moreover, as may be necessary, the operator applies the narrow band light onto the application region, and obtains a narrow band light image.

The operator orients the front end portion 24 toward the tumor $B_1$, projects the treatment tool 62 from the front end of the endoscope 2, and applies the treatment light onto the tumor $B_1$ (see (b) in FIG. 5). As a result of the application of the treatment light, the antibody drug that is bound to the tumor $B_1$ reacts, and the treatment of the tumor $B_1$ is carried out.

Then, the operator orients the front end portion 24 toward the tumor $B_2$, projects the treatment tool 62 from the front end of the endoscope 2, and applies the treatment light onto the tumor $B_2$ (see (c) in FIG. 5). As a result of the application of the treatment light, the antibody drug that is bound to the tumor $B_2$ reacts, and the treatment of the tumor $B_2$ is carried out.

Subsequently, the operator orients the front end portion 24 toward the tumor $B_1$ and applies the narrow band light onto the tumor $B_1$ from the front end of the endoscope 2 (see (d) in FIG. 5). Then, the operator obtains a post-treatment narrow band light image and confirms the effect of treatment on the tumor $B_1$. As far as confirming the effect of treatment is concerned, the operator makes the determination based on the variation between images (explained later).

Subsequently, the operator orients the front end portion 24 toward the tumor $B_2$ and applies the narrow band light onto the tumor $B_2$ from the front end of the endoscope 2 (see (e) in FIG. 5). Then, the operator obtains a post-treatment narrow band light image and confirms the effect of treatment on the tumor $B_2$.

Herein, as may be necessary, the operator again applies the treatment light and confirms the effect of treatment in a repeated manner.

Explained below with reference to FIG. 6 are the operations performed by the processing device 4. FIG. 6 is a flowchart for explaining an example of the operations performed by the processing device according to the first embodiment.

Firstly, before the application of the treatment light, the narrow band light is applied onto the treatment position from the front end portion 24, and a pre-treatment narrow band light image (a first narrow band light image) is obtained (Step S101: narrow-band-light image obtaining process). Herein, the controller 44 causes the light source device 3 to emit the narrow band light, and causes the endoscope 2 to take an image of the narrow band light. After the imaging is performed, the narrow-band-light image generator 412 generates a narrow band light image.

Then, as a result of an operation performed by the operator, the treatment light is applied from the treatment tool 62 onto the antibody drug that is bound to the cancer cells, thereby causing a reaction of the drug (Step S102: drug reaction process). During the drug reaction process, a near-infrared light representing the treatment light is applied onto activate the antibody drug, and the treatment for destroying the cancer cells is carried out.

Subsequently, a narrow band light is applied from the front end portion 24 onto the treatment position and a post-treatment narrow band light image (a second narrow band light image) is obtained (Step S103: narrow-band-light image obtaining process). At Step S103 too, in an identical manner to Step S101, the controller 44 causes the light source device 3 to emit the narrow band light, and causes the endoscope 2 to take an image of the narrow band light.

Herein, the narrow band light and the treatment light are alternately applied from Step S101 to Step S103, thereby enabling holding down the leaking light and enhancing the image quality. Meanwhile, as far as confirming the pre-treatment state and the post-treatment state is concerned, it is desirable to apply the narrow band light before the treatment as well as after the treatment. However, the operations at Steps S101 and S102 can be performed simultaneously, or the operations at Steps S102 and S103 can be performed simultaneously.

Subsequently, the narrow-band-light image variation calculator 413 calculates the variation between the pre-treatment narrow band light image and the post-treatment narrow band light image (Step S104: narrow-band-light image variation calculation process). The narrow-band-light image variation calculator 413 compares the images and calculates, as the image variation, values indicating the intelligibility and the homogeneity of the superficial tissue pattern, and values indicating the homogeneity and visibility of the thickness of the blood vessels.

Figure 7:
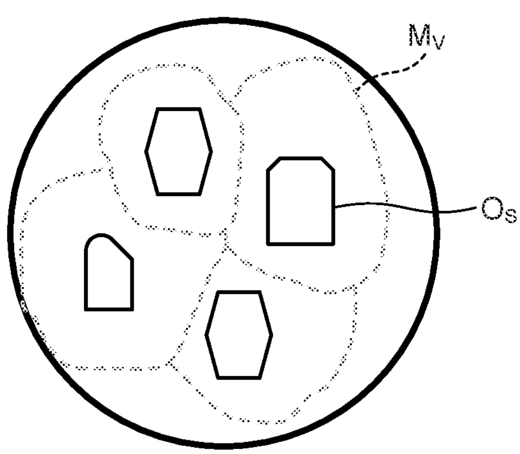
FIG. 7 is a diagram for explaining about the tissue in the normal state.

Given below is the explanation of the state of the tissue visualized as a result of performing NBI observation. FIG. 7 is a diagram for explaining about the tissue in the normal state. In the normal state in which cancer cells are not present, microstructures $O_S$ are uniformly structureless in entirety, and microvessels (in FIG. 7, illustrated as microvessels My using dashed lines) remain invisible.

Figure 8A:
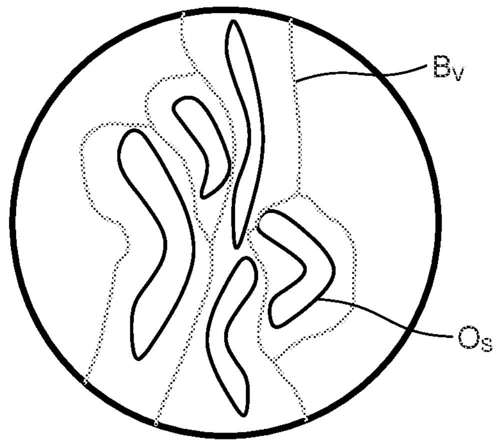
FIG. 8A is a diagram (1) for explaining about the tissue including cancer cells.
Figure 8B:
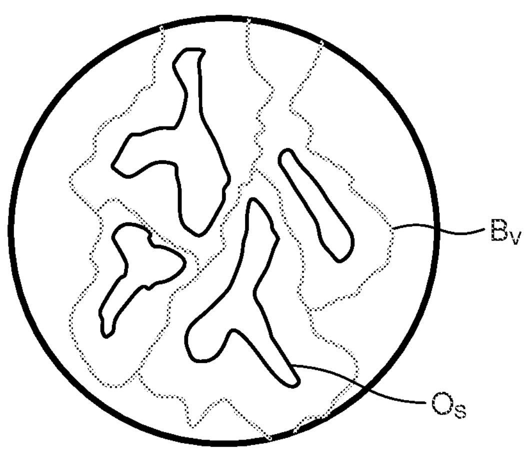
FIG. 8B is a diagram (2) for explaining about the tissue including cancer cells.
Figure 8C:
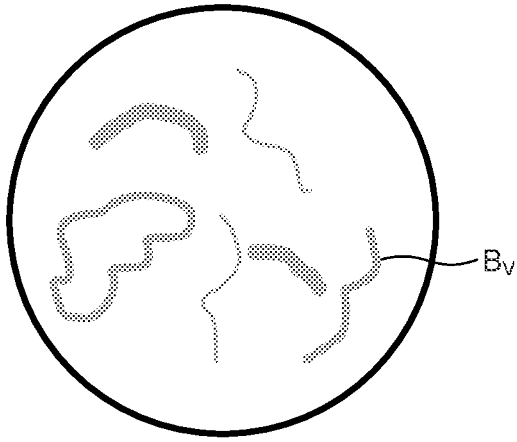
FIG. 8C is a diagram (3) for explaining about the tissue including cancer cells.

FIGS. 8A to 8C are diagrams for explaining about the tissue including cancer cells. In contrast to the normal state illustrated in FIG. 7, in the tissue in which cancer cells are present, the surface pattern of the microstructures $O_S$ and the state of the blood vessels is different as compared to the normal state. For example, as compared to an organized microstructure pattern, a blood vessel pattern may be formed in which blood vessels $B_V$ enclose the microstructures (see FIG. 8A). Alternatively, as compared to an irregular microstructure pattern, a blood vessel pattern may be formed with a mesh design in which the blood vessels $B_V$ enclose the microstructures (see FIG. 8B). Still alternatively, the microstructure pattern may become obscure, and the thickness of the blood vessels $B_V$ may not be uniform (see FIG. 8C).

Figure 9:
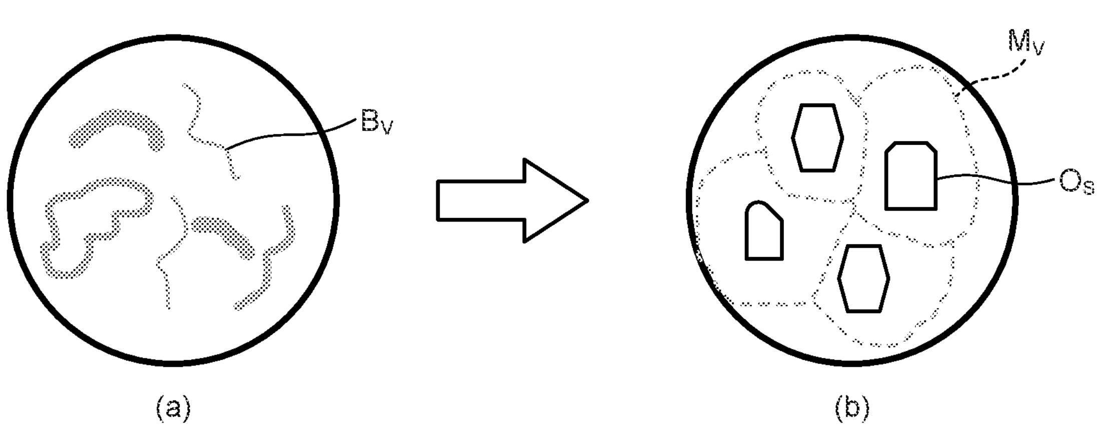
FIG. 9 is a diagram for explaining about the pre-treatment state and the post-treatment state of the tissue.

During photoimmunotherapy, for example, the treatment light is applied onto the tissue illustrated in FIG. 8C, and the normal state illustrated in FIG. 7 is restored. FIG. 9 is a diagram for explaining about the pre-treatment state and the post-treatment state of the tissue. In FIG. (a) in FIG. 9 is illustrated a narrow band light image obtained as a result of performing NBI observation before the treatment. In FIG. (b) in FIG. 9 is illustrated a narrow band light image obtained as a result of performing NBI observation after the treatment. The operator confirms a transition from the state illustrated in (a) in FIG. 9 to the state illustrated in (b) in FIG. 9 in response to the application of the treatment light onto the tissue, and determines the effect of treatment and whether or not the treatment was successful.

At that time, the narrow-band-light image variation calculator 413 individually calculates, from the obtained narrow band light images, the variation occurring either in the state of the vascular structure or in the state of the microstructure $O_S$. The target for calculating the variation can be set by selection from the options, namely, only the vascular structure, only the microstructure, and the vascular structure as well as the microstructure. The narrow-band-light image variation calculator 413 extracts the feature points of an image; compares the variation occurring in the positions of the feature points and compares the sizes and the distribution of the feature points; and calculates the variation.

Figure 10A:
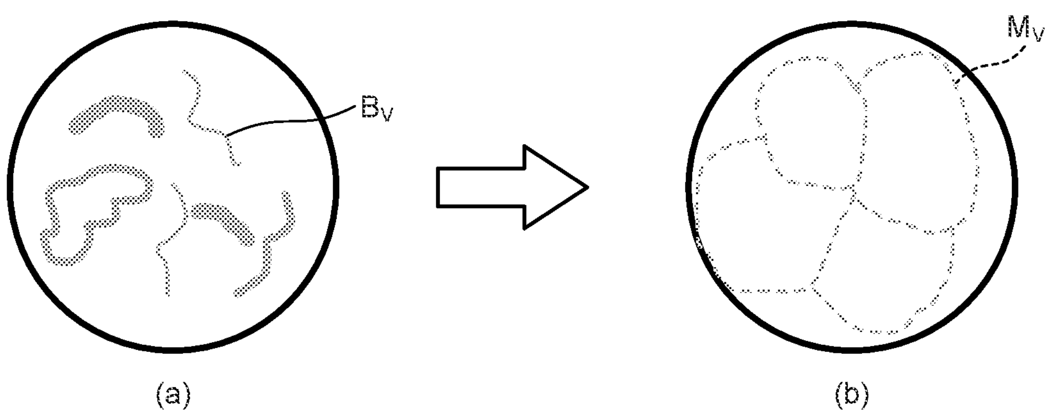
FIG. 10A is a diagram (1) illustrating the extraction of various structures regarding the pre-treatment state and the post-treatment state of the tissue.
Figure 10B:
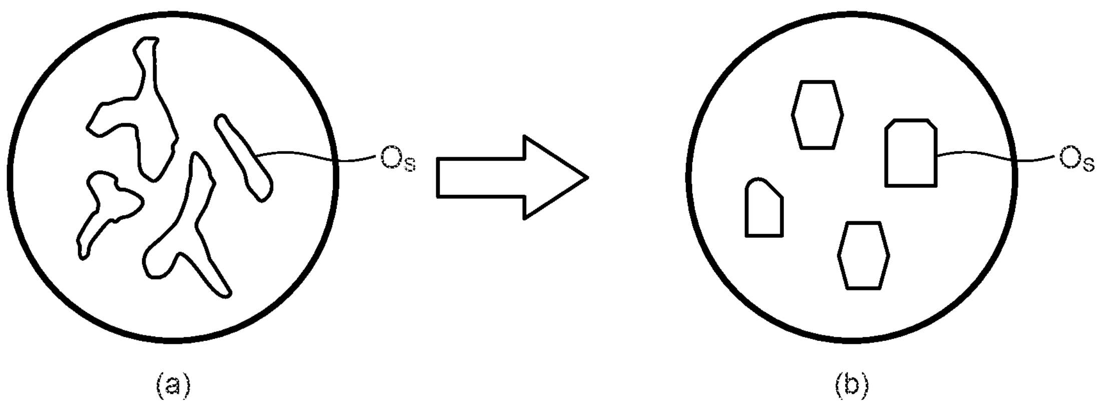
FIG. 10B is a diagram (2) illustrating the extraction of various structures regarding the pre-treatment state and the post-treatment state of the tissue.

FIGS. 10A and 10B are diagrams illustrating the extraction of various structures regarding the pre-treatment state and the post-treatment state of the tissue. In FIG. 10A are illustrated the images when the blood vessels are extracted. In FIG. 10B are illustrated the images when the microstructures are extracted. The narrow-band-light image variation calculator 413 extracts the blood vessels $B_V$ from the pre-treatment narrow band light image as well as from the post-treatment narrow band light image; calculates the contrast value of the blood vessels; and then calculates the contrast ratio between the blood vessels $B_V$ and the surrounding. Subsequently, the narrow-band-light image variation calculator 413 calculates, as the image variation, the difference in the contrast ratios between the pre-treatment narrow band light image and the post-treatment narrow band light image (see FIG. 10A).

Moreover, the narrow-band-light image variation calculator 413 extracts the microstructures $O_S$ of the superficial portion of the mucous membrane from the pre-treatment narrow band light image as well as from the post-treatment narrow band light image; and calculates the intelligibility of the microstructures $O_S$. Then, the narrow-band-light image variation calculator 413 calculates, as the image variation, the difference in the intelligibility between the pre-treatment narrow band light image and the post-treatment narrow band light image (see FIG. 10B). At that time, the post-treatment microstructures are visualized more clearly in in the narrow band light image as compared to the pre-treatment microstructures. Meanwhile, for example, the narrow-band-light image variation calculator 413 can extract the microstructures $O_S$ and calculate, as the variation, the degree of coincidence of the microstructures $O_S$ among the images.

Then, the display image generator 414 generates an image to be displayed in the display 5 (Step S105: display image generation process). The display image generator 414 generates an image in which the variation between the narrow band light images is visually expressed. For example, the display image generator 414 generates a display image that includes an image formed either by lining the pre-treatment narrow band light image and the post-treatment narrow band light image or by superimposing them, and includes visual information indicating the image variation.

The controller 44 displays the image, which is generated at Step S105, in the display 5 (Step S106: display process). As a result of displaying the image in the display 5, the operator is asked to confirm the effect of treatment. The operator looks at the image and confirms the effect of treatment, and accordingly determines whether or not an additional application of the treatment light is to be performed and determines the region for applying the treatment light. Then, the operator operates the input portion 43 and inputs the determination result.

Figure 11:
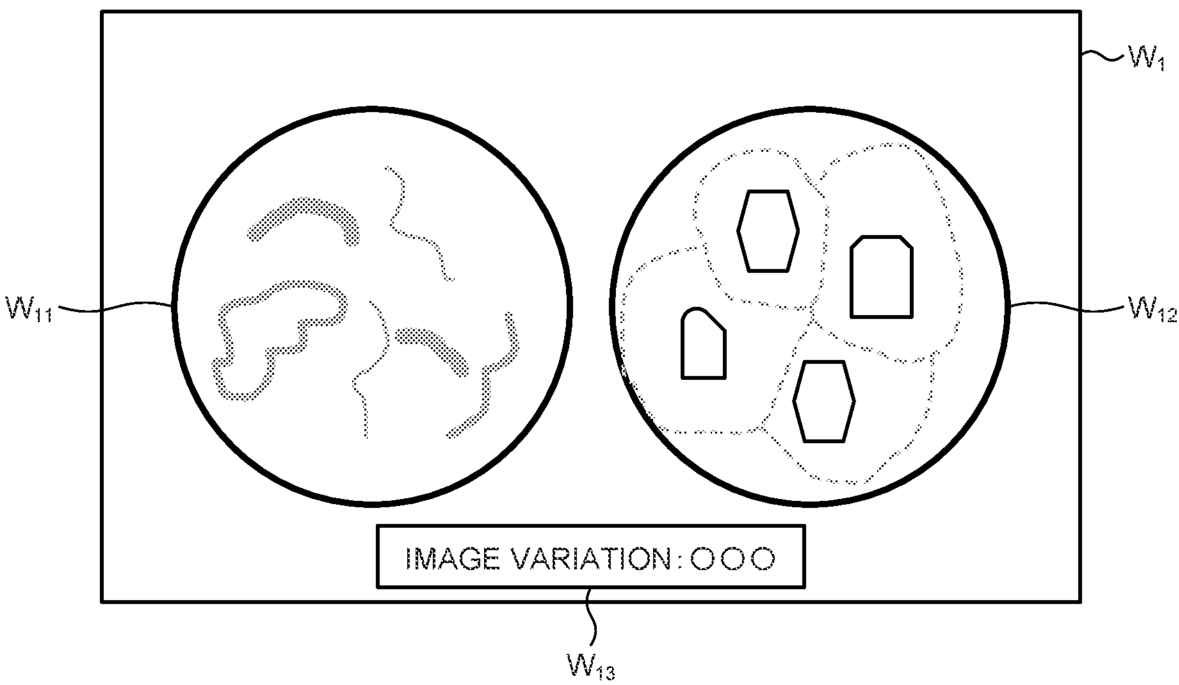
FIG. 11 is a diagram (1) illustrating an example of a display screen in which images indicating the pre-treatment state and the post-treatment state of the tissue are displayed.
Figure 12:
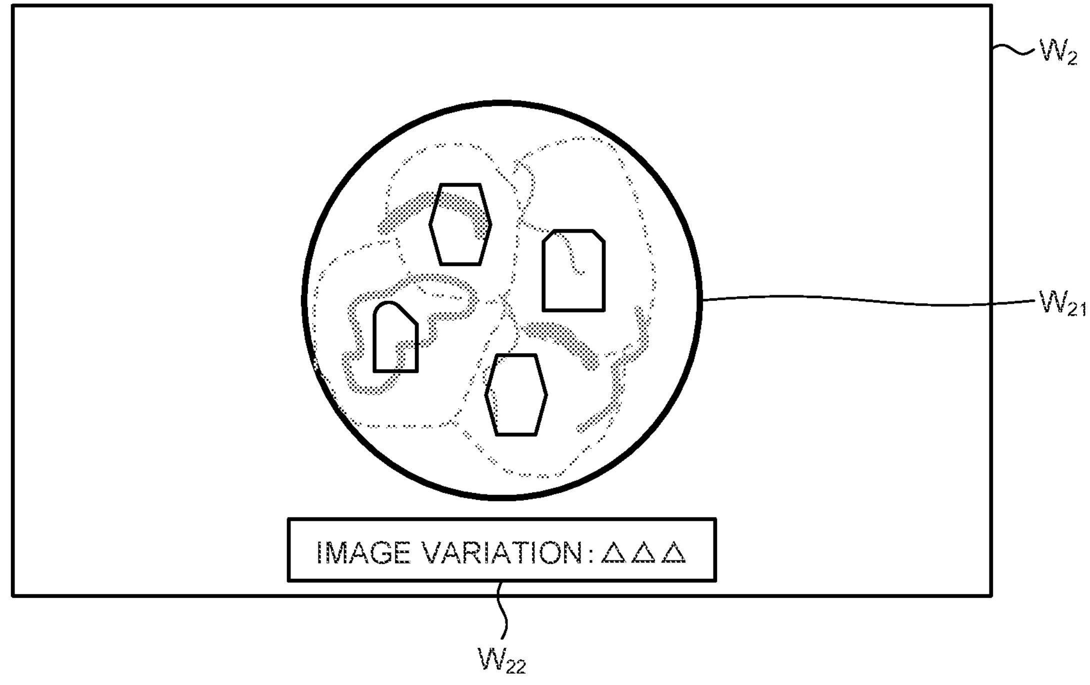
FIG. 12 is a diagram (2) illustrating an example of the display screen in which images indicating the pre-treatment state and the post-treatment state of the tissue are displayed.

FIGS. 11 and 12 are diagrams illustrating examples of a display screen in which images indicating the pre-treatment state and the post-treatment state of the tissue are displayed. For example, in the display 5, a display image $W_1$ is displayed that includes: a first narrow-band-light image display portion $W_{11}$ for displaying the pre-treatment narrow band light image; a second narrow-band-light image display portion $W_{12}$ for displaying the post-treatment narrow band light image; and an information display portion $W_{13}$ for displaying the variation (for example, the contrast value mentioned earlier) between the pre-treatment narrow band light image and the post-treatment narrow band light image (see FIG. 11). Moreover, for example, in the display 5, a display image $W_2$ is displayed that includes: an image display portion $W_2$ for displaying the pre-treatment narrow band light image and the post-treatment narrow band light image in a superimposed manner; and an information display portion $W_{22}$ for displaying the variation between the pre-treatment narrow band light image and the post-treatment narrow band light image (see FIG. 12). At that time, the size of the narrow band light images displayed side-by-side can be set in an appropriate manner, or the transmittance of the narrow band light images at the time of superimposition can be set in an appropriate manner.

When the input portion 43 receives input of the determination result, the controller 44 determines whether or not an additional application of the treatment light is to be performed (Step S107). Based on the input determination result, if it is determined that the additional application of the treatment light is not required (No at Step S107), then the operations are ended. On the other hand, if it is determined that the additional application of the treatment light is required (Yes at Step S107), then the system control proceeds to Step S108.

In the case of performing the additional application of the treatment light, for example, in the illumination optical system, control is performed to match the shape of the light application range to the shape of the boundary region, and the operator adjusts the spot diameter and applies the treatment light.

The controller 44 determines whether or not, in the region on which the additional application of the treatment light is to be performed, the amount of already-applied light is within the acceptable range (Step S108). The acceptable range represents a preset amount of light and is set to have at least the upper limit value. The upper limit value is set so as to hold down any damage to the tissue due to excessive application of the treatment light. Thus, for example, the controller 44 determines whether or not the amount of light already applied onto the operator-specified target region (i.e., the cumulative amount of light) is exceeding the upper limit value.

If the controller 44 determines that the amount of light is within the acceptable range (i.e., smaller than the upper limit value) (Yes at Step S108), then the system control returns to Step S102 and the operations are repeated. At that time, from among the narrow band light images obtained before newly the implementing drug reaction process (Step S102), the latest narrow band light image is treated as the first narrow band light image before the treatment; and the narrow band light image obtained after the drug reaction process is treated as the second narrow band light image.

Meanwhile, if the controller 44 determines that the amount of already-applied light is exceeding the acceptable range (the upper limit value) (No at Step S108), then the system control proceeds to Step S109.

At Step S109, the controller 44 outputs an alert indicating that the amount of applied light has exceeded the acceptable range. The alert can be displayed as character information in the display 5, or can be issued in the form of a sound or a light, or can be a combination thereof. After the alert is displayed in the display 5, the controller 44 ends the operations.

In the first embodiment described above, narrow band light images are used to calculate the variation in the pre-treatment tissue and the post-treatment tissue, and the variation therebetween is displayed. Then, the operator is asked to determine whether or not the additional application of the treatment light is to be performed. According to the first embodiment, regarding the variation in the tissue or the blood vessels before and after the treatment, the effect of treatment is calculated at the tissue level based on the narrow band light images in which the tissue and the blood vessels are visualized. That enables appropriate application of light onto the treatment region.

Moreover, in the first embodiment, after the effect of treatment is confirmed according to the fluorescence, at the time of additional application of the treatment light, the cumulative amount of treatment light applied onto the concerned region is compared with the acceptable range. If the cumulative amount of treatment light has exceeded the acceptable range, then an alert is issued to indicate that the cumulative amount of treatment light has exceeded the acceptable range. Thus, according to the first embodiment, it becomes possible to hold down the damage to the tissue due to excessive application of the treatment light.

Meanwhile, in the first embodiment, the imaging element 244 can be configured using a multi-band image sensor, so that the lights having a plurality of mutually different wavelength bands can be individually obtained. For example, the scattering light or the returning light of the light having the wavelength band equal to or greater than 380 nm and equal to or smaller than 440 nm, and the scattering light or the returning light of the light having the wavelength band equal to or greater than 530 nm and equal to or smaller than 550 nm can be individually obtained using a multi-band image sensor; and a narrow band light image corresponding to each light can be generated. As a result, it becomes possible to obtain blood vessel images having different depths from the superficial portion of the mucous membrane, and to calculate the image variation with a higher degree of accuracy using the images of the blood vessels and the tissue at each depth.

Second Embodiment

Figure 13:
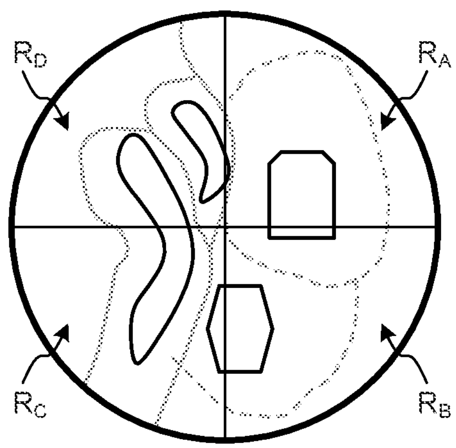
FIG. 13 is a diagram for explaining about a determination operation for determining the effect of treatment according to a second embodiment of the disclosure.

A second embodiment is described below with reference to FIG. 13. An endoscope system according to the second embodiment is identical to the endoscope system 1 according to the first embodiment. Hence, the same explanation is not given again. The following explanation is given about the operations that are different than the operations according to the first embodiment.

In the second embodiment, the narrow-band-light image variation calculator 413 divides a narrow band light image into a plurality of regions, and calculates the image variation occurring in each region. FIG. 13 is a diagram for explaining about a determination operation for determining the effect of treatment according to the second embodiment of the disclosure. In the example illustrated in FIG. 13, the narrow-band-light image variation calculator 413 divides the pre-treatment narrow band light image as well as the post-treatment narrow band light image into four regions ($R_A$ to $R_D$), and calculates the image variation occurring in each region. In FIG. 13, the tissue in the regions $R_A$ and $R_B$ are in the normal state as a result of the treatment, but the tissue in the regions $R_C$ and $R_D$ still includes cancer cells even after the treatment. The operator observes the narrow band light images and the image variation, and determines whether or not the additional application of the treatment light is to be performed in any region.

In the second embodiment described above, in an identical manner to the first embodiment, the variation between the pre-treatment tissue and the post-treatment tissue is calculated using the narrow band light images, and the variation is displayed. Then, the operator is asked to determine whether or not the additional application of the treatment light is to be performed. According to the second embodiment, regarding the variation in the tissue or the blood vessels before and after the treatment, the effect of treatment is calculated at the tissue level based on the narrow band light images in which the tissue and the blood vessels are visualized. That enables appropriate application of light onto the treatment region.

Moreover, according to the second embodiment, the narrow band light images are divided into a plurality of regions, and the image variation occurring in each region is calculated. Hence, it becomes possible to hold down excessive application of the treatment light onto the regions in which the treatment is complete. At the same time, the treatment light can be continually applied onto the regions in which the treatment is not yet complete.

Third Embodiment

A third embodiment is described below with reference to FIG. 14. FIG. 14 is a block diagram illustrating an overall configuration of an endoscope system according to the third embodiment of the disclosure. An endoscope system 1A according to the third embodiment includes a processing device 4A in place of the processing device 4 of the endoscope system 1 according to the first embodiment. Other than the processing device 4A, the configuration is same as the endoscope system 1. Hence, the same explanation is not given again.

Given below is the explanation of a configuration of the processing device 4A. The processing device 4A includes an image processor 41A, the synchronization signal generator 42, the input portion 43, the controller 44, and the storage 45.

The image processor 41A includes the white light image generator 411, the narrow-band-light image generator 412, the narrow-band-light image variation calculator 413, the display image generator 414, and a calculator 415.

The calculator 415 estimates the effect of treatment based on the image variation calculated by the narrow-band-light image variation calculator 413. For example, the calculator 415 calculates the difference in the contrast values that are calculated as the image variation between the pre-treatment narrow band light image and the post-treatment narrow band light image; compares the difference with a preset threshold value; and estimates the effect of treatment. If the difference is smaller than the threshold value, then the calculator 415 estimates that the additional application of the treatment light is required. On the other hand, if the difference is equal to or greater than the threshold value, then the calculator 415 estimates that the treatment is complete. The estimation operation can be performed as the operation at Step S107 illustrated in FIG. 6. Alternatively, the estimation operation can be performed as part of the variation calculation operation at Step S104, and the estimation result can be displayed during the display process at Step S106.

In the case of displaying the estimation result during the display process at Step S106, the display image generator 414 generates images by replacing the information displayed in the information display portions $W_{13}$ and $W_{22}$ in the display images $W_1$ and $W_2$, respectively, illustrated in FIGS. 11 and 12, respectively, with the estimation result. Alternatively, the estimation result as well as the information about the image variation can be displayed in the images.

In the third embodiment described above, in an identical manner to the first embodiment, the variation between the pre-treatment tissue and the post-treatment tissue is calculated using the narrow band light images, and the variation is displayed. Then, the operator is asked to determine whether or not additional application of the treatment light is to be performed. According to the third embodiment, regarding the variation in the tissue or the blood vessels before and after the treatment, the effect of treatment is calculated at the tissue level based on the narrow band light images in which the tissue and the blood vessels are visualized. That enables appropriate application of light onto the treatment region.

Moreover, in the third embodiment, the effect of treatment is estimated from the variation between the narrow band light images; and that estimation result can serve as the preferred determination criterion at the time of determining the effect of treatment by observing the narrow band light images and the image variation.

Fourth Embodiment

Figure 15A:
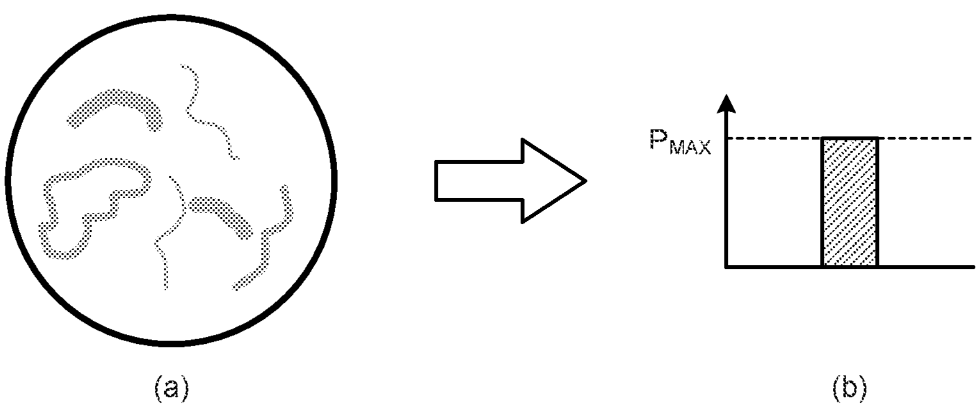
FIG. 15A is a diagram (1) for explaining an estimation operation performed according to a fourth embodiment of the disclosure.
Figure 15B:
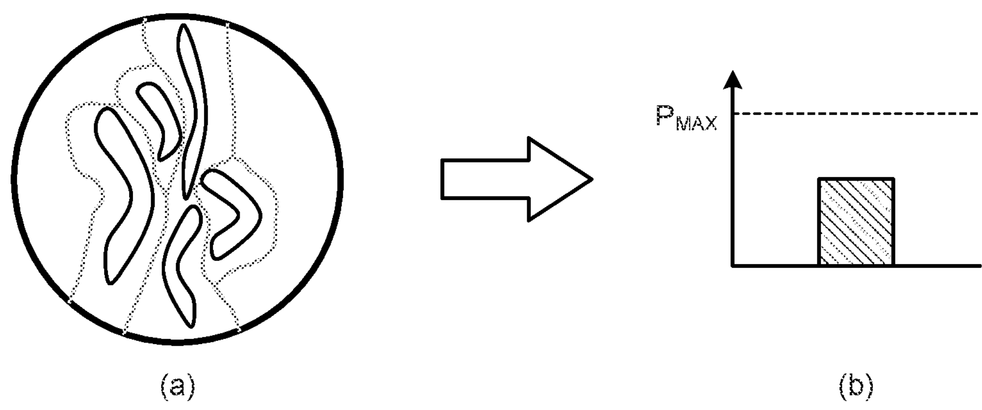
FIG. 15B is a diagram (2) for explaining the estimation operation performed according to the fourth embodiment of the disclosure.

A fourth embodiment is described below with reference to FIGS. 15A and 15B. An endoscope system according to the fourth embodiment is identical to the endoscope system 1A according to the third embodiment. Hence, the same explanation is not given again. The following explanation is given about the operations that are different than the operations according to the third embodiment.

In the fourth embodiment, the narrow-band-light image variation calculator 413 either calculates the variation between the pre-treatment narrow band light image and the post-treatment narrow band light image, or calculates the image variation between the pre-treatment narrow band light image and a narrow band light image of the normal tissue as obtained in advance.

Based on the image variation calculated by the narrow-band-light image variation calculator 413, the calculator 415 estimates the output (application intensity) of the treatment light. FIGS. 15A and 15B are diagrams for explaining an estimation operation performed according to the fourth embodiment of the disclosure. The calculator 415 estimates the intensity of the treatment light based on the magnitude of the image variation. For example, in the narrow band light image illustrated in (a) in FIG. 15A, when there is a large image variation with respect to the normal tissue, the calculator 415 sets the output of the treatment light to a maximum value $P_{MAX}$ (see (b) in FIG. 15A). In the narrow band light image illustrated in (a) in FIG. 15B, when there is only a small image variation with respect to the normal tissue, the calculator 415 sets the output of the treatment light to a smaller value than the maximum value $P_{MAX}$ (see (b) in FIG. 15B). At that time, a threshold value corresponding to the output value is set in advance with respect to the image variation. This estimation operation is either performed before the drug reaction process at Step S102 illustrated in FIG. 6, or performed after it is determined at Step S107 that the additional application of the treatment light is required (Yes at Step S107).

In the case of displaying the estimation result, the display image generator 414 generates images by displaying information indicating the output of the treatment light as the estimation result in the information display portions $W_{13}$ and $W_{22}$ in the display images $W_1$ and $W_2$, respectively, illustrated in FIGS. 11 and 12, respectively. Alternatively, the estimation result as well as the information about the image variation can be displayed in the images.

The operator observes the narrow band light images and the image variation as well as refers to the estimated output value of the treatment light, and determines whether or not the additional application of the treatment light is to be performed in any region and determines the output (energy) of the treatment light.

In the fourth embodiment described above, in an identical manner to the first embodiment, the variation between the pre-treatment tissue and the post-treatment tissue is calculated using the narrow band light images, and the variation is displayed. Then, the operator is asked to determine whether or not the additional application of the treatment light is to be performed. According to the fourth embodiment, regarding the variation in the tissue or the blood vessels before and after the treatment, the effect of treatment is calculated at the tissue level based on the narrow band light images in which the tissue and the blood vessels are visualized. That enables appropriate application of light onto the treatment region.

Moreover, according to the fourth embodiment, the output of the treatment light is estimated based on the narrow band light images, and the estimation result can serve as the preferred determination criterion at the time of applying the treatment light.

Fifth Embodiment

A fifth embodiment is explained below with reference to FIGS. 16A and 16B. An endoscope system according to the fifth embodiment is identical to the endoscope system 1A according to the third embodiment. Hence, the same explanation is not given again. The following explanation is given about the operations that are different than the operations according to the third embodiment.

In the fifth embodiment, the narrow-band-light image variation calculator 413 either calculates the variation between the pre-treatment narrow band light image and the post-treatment narrow band light image, or calculates the image variation between the pre-treatment narrow band light image and a narrow band light image of the normal tissue as obtained in advance.

Based on the image variation calculated by the narrow-band-light image variation calculator 413, the calculator 415 estimates the required application intensity of the treatment light. FIGS. 16A and 16B are diagrams for explaining an estimation operation performed according to the fifth embodiment of the disclosure. The calculator 415 estimates the application period of the treatment light based on the magnitude of the image variation. At that time, the treatment light is assumed to be at a preset output. For example, in the narrow band light image illustrated in (a) in FIG. 16A, when there is a large image variation with respect to the normal tissue, the calculator 415 sets the application period to, for example, 70 minutes according to the magnitude of the image variation. In the narrow band light image illustrated in (a) in FIG. 16B, when there is only a small image variation with respect to the normal tissue, the calculator 415 sets the application period to, for example, 15 minutes. At that time, a threshold value corresponding to the application period is set in advance with respect to the image variation. This estimation operation is either performed before the drug reaction process at Step S102 illustrated in FIG. 6, or performed after it is determined at Step S107 that the additional application of the treatment light is required (Yes at Step S107).

Figure 16A:
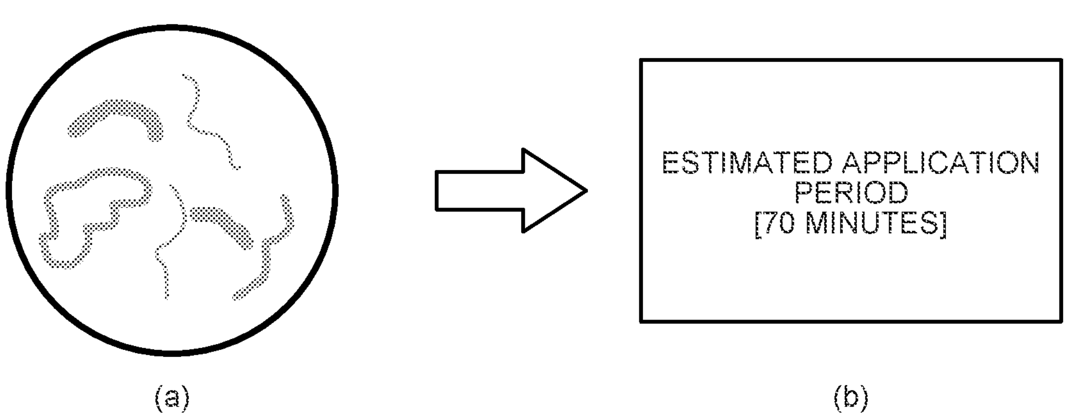
FIG. 16A is a diagram (1) for explaining an estimation operation performed according to a fifth embodiment of the disclosure.
Figure 16B:
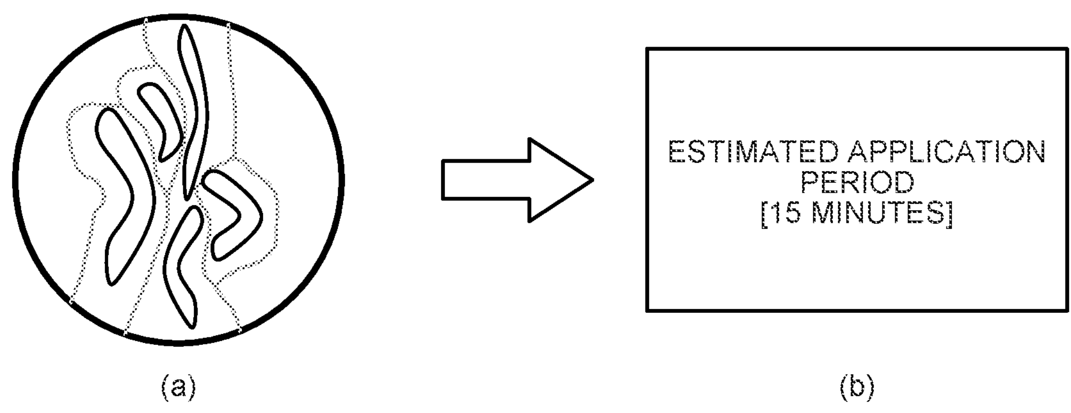
FIG. 16B is a diagram (2) for explaining the estimation operation performed according to the fifth embodiment of the disclosure.

In the case of displaying the estimation result, the display image generator 414 generates images by displaying information indicating the application period of the treatment light as the estimation result in the information display portions $W_{13}$ and $W_{22}$ in the display images $W_1$ and $W_2$, respectively, illustrated in FIGS. 11 and 12, respectively (for example, see (b) in FIG. 16A and (b) in FIG. 16B). Alternatively, the estimation result as well as the information about the image variation can be displayed in the images.

The operator observes the narrow band light images and the image variation as well as refers to the estimated application period of the treatment light, and determines whether or not the additional application of the treatment light is to be performed in any region and determines the application period of the treatment light.

In the fifth embodiment described above, in an identical manner to the first embodiment, the variation between the pre-treatment tissue and the post-treatment tissue is calculated using the narrow band light images, and the variation is displayed. Then, the operator is asked to determine whether or not the additional application of the treatment light is to be performed. According to the fifth embodiment, regarding the variation in the tissue or the blood vessels before and after the treatment, the effect of treatment is calculated at the tissue level based on the narrow band light images in which the tissue and the blood vessels are visualized. That enables appropriate application of light onto the treatment region.

Moreover, according to the fifth embodiment, the treatment light application period is estimated based on the narrow band light images, and the estimation result can serve as the preferred determination criterion at the time of applying the treatment light.

Meanwhile, the fifth embodiment can be combined with the fourth embodiment, and the output of the treatment light and the application period of the treatment light can be combinedly output as the estimation result.

Moreover, in the fourth and fifth embodiments described above, a narrow band light image meant for comparison can be prepared in advance in a corresponding manner to the output of the treatment light or the application period of the treatment light, and the calculator 415 can compare the features of the narrow band light image meant for comparison and the feature quantity of the narrow band light image to be processed, and accordingly estimate the output of the treatment light or the application period of the treatment light.

Sixth Embodiment

A sixth embodiment is described below with reference to FIG. 17. FIG. 17 is a block diagram illustrating an overall configuration of an endoscope system according to a sixth embodiment of the disclosure. An endoscope system 1B according to the sixth embodiment has an identical configuration to the configuration of the endoscope system 1 according to the first embodiment. In the endoscope system 1B, the processing device 4 is electrically connected to the treatment tool device 6, and the controller 44 of the processing device 4 controls the emission of the treatment light from the treatment tool 62.

In the case of implementing photoimmunotherapy, the processing device 4 performs operations according to the flow illustrated in FIG. 6. At the time of applying the treatment light, the controller 44 controls the application range, the application timing, and the application period of the treatment light. More particularly, for example, with respect to the application range set by the operator, the controller 44 sets a light intensity (output value) representing a preset amount of applied light, and sets the application period. In response to the pressing of a switch of the operation input portion 611, the controller 44 starts the application control of the treatment light. At the time of additional application of the treatment light, the controller 44 sets the shape of the application range of the treatment light, which is emitted from the treatment tool 62, according to the target boundary region; and, in response to the pressing of a switch of the operation input portion 611, starts the application control of the treatment light.

Meanwhile, in the sixth embodiment, the controller 44 performs control to ensure that the narrow band light and the treatment light are alternately emitted according to the flow illustrated in FIG. 6. Alternatively, the narrow band light and the treatment light can be emitted in a simultaneous manner.

In the first to sixth embodiments described above, the explanation is given about the example in which the light source device 3 and the processing device 4 are separate devices. Alternatively, the light source device 3 and the processing device 4 can be integrated into a single device. Moreover, in the first to sixth embodiments, described above, the explanation is given about the example in which the treatment light is applied using a treatment tool. Alternatively, the light source device 3 can be configured to emit the treatment light.

In the first to sixth embodiments described above, with the aim of confirming the effect of treatment based on the fluorescence intensity, an excitation light can be emitted for causing excitation of the excitation target (for example, an antibody drug used in photoimmunotherapy). For example, the light source device 3 includes an excitation light source implemented using an LED light source or a laser light source. The excitation light and the treatment light either can have the same frequency band (the same central frequency), or can have mutually different frequency bands (central frequencies). Meanwhile, when the excitation light is used in common with the treatment light, it serves the purpose as long as the treatment light (the excitation light) is applied using the treatment tool 62 or the excitation light source. Hence, either the excitation light source 313 or the treatment tool 62 can be omitted from the configuration. In the case of causing excitation of an antibody drug in photoimmunotherapy, for example, the near-infrared light $L_P$ having the central wavelength of 690 nm is used.

Moreover, in the first to sixth embodiments described above, the endoscope system 1, which treats the body tissue inside a subject as the observation target and which includes the flexible endoscope 2, represents the endoscope system according to the disclosure.

Alternatively, it is also possible to use an endoscope system in which a rigid endoscope is used, or an industrial endoscope is used for observing the characteristic features of materials, or a fiberscope is used, or such a device is used in which a camera head is connected to the eyepiece of an optical endoscope such as an optical viewing tube.

Note

A phototherapy method including:

administering a drug, which is to be used in phototherapy, to a treatment area;

applying narrow band light onto the treatment area to obtain a pre-treatment narrow band light image;

applying treatment light onto the treatment area to cause the drug, which is bound to the treatment area, to react;

applying narrow band light onto the treatment area to obtain a post-treatment narrow band light image;

calculating a time variation between the pre-treatment narrow band light image and the post-treatment narrow band light image; and using the time variation between the pre-treatment narrow band light image and the post-treatment narrow band light image to determine whether or not to continue an application of the treatment light.

As explained above, a phototherapy device, a phototherapy method, and a computer-readable recording medium according to the disclosure are useful in confirming the effect of treatment in an appropriate manner.

According to the disclosure, it becomes possible to confirm the effect of treatment in an appropriate manner.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A phototherapy device comprising:

a treatment light emitter configured to emit treatment light for causing a reaction of a drug;

a narrow band light emitter configured to emit narrow band light having part of wavelength band of a visible light range;

an imager configured to obtain a narrow band light image which is formed using the narrow band light applied onto an application position of the treatment light;

a narrow-band-light image variation calculator configured to:

compare a first narrow band light image obtained before an application of the treatment light with a second narrow band light image obtained after the application of the treatment light;

extract a blood vessel structure from each of the first narrow band light image and the second narrow band light image;

calculate a contrast ratio between the extracted blood vessel structure and surrounding tissue in each image; and calculate, as a variation over time, a difference in contrast ratios;

a display image generator configured to generate a display image including information based on the calculated variation over time, wherein:

the narrow band light comprises a wavelength band equal to or greater than 390 nm and equal to or smaller than 445 nm and a wavelength band equal to or greater than 530 nm and equal to or smaller than 550 nm.

2. The phototherapy device according to claim 1, further comprising a controller configured to control an emission of the treatment light and an emission of the narrow band light at mutually different timings and at mutually nonoverlapping timings.

3. The phototherapy device according to claim 1, wherein the narrow-band-light image variation calculator is configured to divide the each of the first narrow band light image and second narrow band light image into a plurality of regions, and calculate an amount of variation occurring in an image in each region obtained by division.

4. The phototherapy device according to claim 1, wherein the display image generator is configured to generate a display image in which the first narrow band light image obtained before the application of the treatment light is lined up with the second narrow band light image obtained after the application of the treatment light.

5. The phototherapy device according to claim 1, wherein the display image generator generates a display image in which the first narrow band light image obtained before application of the treatment light and the second narrow band light image obtained after application of the treatment light are superimposed.

6. The phototherapy device according to claim 1, further comprising a treatment light calculator configured to estimate an output of the treatment light based on the variation over time calculated by the narrow-band-light image variation calculator.

7. The phototherapy device according to claim 1, further comprising a treatment light calculator configured to estimate an application period of the treatment light based on the variation over time calculated by the narrow-band-light image variation calculator.

8. A phototherapy device comprising:

a treatment light emitter configured to emit treatment light for causing a reaction of a drug;

a narrow band light emitter configured to emit narrow band light having part of wavelength band of a visible light range;

an imager configured to obtain a narrow band light image which is formed using the narrow band light applied onto an application position of the treatment light;

a narrow-band-light image variation calculator configured to:

compare a first narrow band light image obtained before an application of the treatment light with a second narrow band light image obtained after the application of the treatment light;

extract a structure of mucous surface from each of the first narrow band light image and second narrow band light image;

calculate, as a variation over time, a difference in intelligibility of the extracted structure of mucous surface;

a display image generator configured to generate a display image including information based on the calculated variation over time, wherein the narrow band light comprises a wavelength band equal to or greater than 390 nm and equal to or smaller than 445 nm and a wavelength band equal to or greater than 530 nm and equal to or smaller than 550 nm.

9. The phototherapy device according to claim 8, further comprising a controller configured to control an emission of the treatment light and an emission of the narrow band light at mutually different timings and at mutually nonoverlapping timings.

10. The phototherapy device according to claim 8, wherein the narrow-band-light image variation calculator is configured to divide the each of the first narrow band light image and second narrow band light image into a plurality of regions, and calculate an amount of variation occurring in an image in each region obtained by division.

11. The phototherapy device according to claim 8, wherein the display image generator generates a display image in which the first narrow band light image obtained before application of the treatment light and the second narrow band light image obtained after application of the treatment light are superimposed.

12. The phototherapy device according to claim 8, further comprising a treatment light calculator configured to estimate an output of the treatment light based on the variation over time calculated by the narrow-band-light image variation calculator.

13. The phototherapy device according to claim 8, further comprising a treatment light calculator configured to estimate an application period of the treatment light based on the variation over time calculated by the narrow-band-light image variation calculator.

14. A phototherapy device comprising:

a treatment light emitter configured to emit treatment light for causing a reaction of a drug;

a narrow band light emitter configured to emit narrow band light having part of wavelength band of a visible light range;

an imager configured to obtain a narrow band light image which is formed using the narrow band light applied onto an application position of the treatment light;

a narrow-band-light image variation calculator configured to:

compare a first narrow band light image obtained before an application of the treatment light with a second narrow band light image obtained after the application of the treatment light;

extract a structure of mucous surface from each of the first narrow band light image and second narrow band light image; and calculate as a variation over time, a difference in homogeneity of the extracted structure of mucous surface;

a display image generator configured to generate a display image including information based on the calculated variation over time, wherein the narrow band light has a wavelength band equal to or greater than 390 nm and equal to or smaller than 445 nm and a wavelength band equal to or greater than 530 nm and equal to or smaller than 550 nm.

15. The phototherapy device according to claim 14, further comprising a controller configured to control an emission of the treatment light and an emission of the narrow band light at mutually different timings and at mutually nonoverlapping timings.

16. The phototherapy device according to claim 14, wherein the narrow-band-light image variation calculator is configured to divide the each of the first narrow band light image and second narrow band light image into a plurality of regions, and calculate an amount of variation occurring in an image in each region obtained by division.

17. The phototherapy device according to claim 14, wherein the display image generator generates a display image in which the first narrow band light image obtained before application of the treatment light and the second narrow band light image obtained after application of the treatment light are superimposed.

18. The phototherapy device according to claim 14, further comprising a treatment light calculator configured to estimate an output of the treatment light based on the variation over time calculated by the narrow-band-light image variation calculator.

19. The phototherapy device according to claim 14, further comprising a treatment light calculator configured to estimate an application period of the treatment light based on the variation over time calculated by the narrow-band-light image variation calculator.

* * * * *